United States Patent
Haikala et al.

[11] Patent Number: 5,122,524
[45] Date of Patent: Jun. 16, 1992

[54] TRIAZINONE COMPOUNDS COMPOSITIONS THEREOF AND METAL OF USE

[75] Inventors: Heimo O. Haikala, Espoo; Erkki J. Honkanen, Vantaa; Kari K. Lönnberg, Routio; Pentti T. Nore, Helsinki; Jarmo J. Pystynen, Espoo; Anne M. Luiro, Helsinki; Aino K. Pippuri, Espoo, all of Finland

[73] Assignee: Orion-yhtymä Oy, Espoo, Finland

[21] Appl. No.: 670,338

[22] Filed: Mar. 15, 1991

Related U.S. Application Data

[62] Division of Ser. No. 477,530, Feb. 9, 1990, Pat. No. 5,019,575.

[30] Foreign Application Priority Data

Feb. 11, 1989 [GB] United Kingdom ............... 8903130

[51] Int. Cl.⁵ .................. A61K 31/53; C07D 253/06
[52] U.S. Cl. ................... 514/242; 514/222.5; 514/229.2; 544/8; 544/66; 544/182; 544/239
[58] Field of Search ............... 544/182; 514/242

[56] References Cited

U.S. PATENT DOCUMENTS

| | | | |
|---|---|---|---|
| 4,353,905 | 10/1982 | Sircar et al. | 514/252 |
| 4,581,356 | 4/1986 | Teraji et al. | 514/242 |
| 4,584,298 | 4/1986 | Brown et al. | 514/242 |
| 4,599,332 | 7/1986 | Sircar | 514/247 |
| 4,616,015 | 10/1986 | Teraji | 514/242 |
| 4,618,610 | 10/1986 | Teraji et al. | 514/242 |
| 4,656,170 | 4/1987 | Sircar | 514/247 |
| 4,898,862 | 2/1990 | Morisawa et al. | 514/242 |
| 5,019,575 | 5/1991 | Haikala et al. | 514/242 |

FOREIGN PATENT DOCUMENTS

| | | |
|---|---|---|
| 0052442 | 5/1982 | European Pat. Off. . |
| 0208518 | 1/1987 | European Pat. Off. . |
| 223937 | 6/1987 | European Pat. Off. . |

OTHER PUBLICATIONS

Ege et al., *J. Liebigs Ann. Chem.* pp. 791–799 (1977).
Hudson et al., *J. Org. Chem.* 28, pp. 2246–2247 (1963).
Curran et al., *J. Med. Chem.* 17, pp. 273–281 (1974).

*Primary Examiner*—Mukund J. Shaw
*Assistant Examiner*—E. Beinhardt
*Attorney, Agent, or Firm*—Burns, Doane, Swecker & Mathis

[57] ABSTRACT

New heterocyclic compounds of formula I

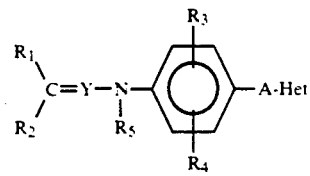

in which Het means one of following groups;

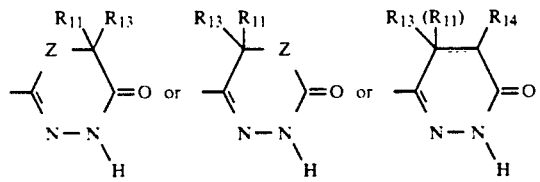

wherein $R_{11}$, $R_{13}$ and $R_{14}$ mean independently hydrogen, hydroxymethyl or lower alkyl group, Z means S, O or NH; A means valency bond, $-CH=CH-$, or $-CH_2-CH_2-$ group; $R_1$ and $R_2$ independently mean nitro, cyano, halogen, amino, carboxamido, aryl, aroyl, pyridyl, alkoxycarbonyl, acyl or one of following groups;

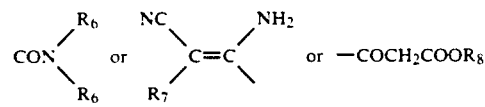

wherein $R_6$ means hydrogen or lower alkyl group, $R_8$ means lower alkyl, $R_7$ means cyano or $COOR_{10}$, wherein $R_{10}$ means hydrogen or lower alkyl or $R_1$ and $R_2$ together form a substituted or unsubstituted 5 or 6 membered ring which may contain 1 or 2 heteroatom N; $R_3$, $R_4$, and $R_5$ mean independently hydrogen, hydroxy or lower alkyl group; Y means N or CH. The compounds may be used in the treatment of congestive heart failure.

10 Claims, No Drawings

TRIAZINONE COMPOUNDS COMPOSITIONS THEREOF AND METAL OF USE

This application is a divisional of application Ser. No. 07/477,530, filed Feb. 9, 1990, now U.S. Pat. No. 5,019,575.

The present invention relates to new heterocyclic compounds and salts thereof as well as new intermediates. The invention also relates to compositions containing these compounds and to a process for the preparation of the same.

The present compounds are useful as cardiotonic agents, antihypertensive agents and vasodilators for the treatment of congestive heart failure. The compounds are new.

The new compounds according to the present invention are heterocyclic compounds of formula I

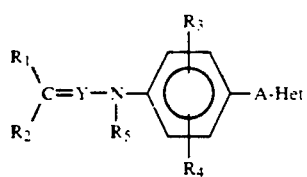

wherein Het means one of following groups:

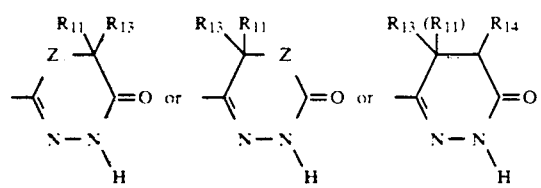

wherein $R_{11}$, $R_{13}$ and $R_{14}$ mean independently hydrogen or lower alkyl group, Z means S, O or NH; A means valency bond, —CH=CH— or —CH$_2$—CH$_2$— group; $R_1$ and $R_2$ independently mean nitro, cyano, halogen, amino, carboxamido, aryl, aroyl, pyridyl, alkoxycarbonyl, acyl or one of following groups:

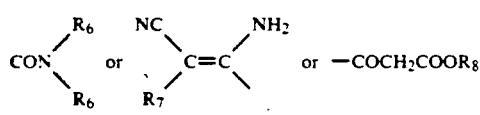

wherein $R_6$ means hydrogen or lower alkyl group, $R_8$ means lower alkyl, $R_7$ means cyano or $COOR_{10}$, wherein $R_{10}$ means hydrogen or lower alkyl or $R_1$ and $R_2$ together form a substituted or unsubstituted 5 or 6 membered ring which may contain 1 or 2 heteroatom N; $R_3$, $R_4$, and $R_5$ mean independently hydrogen, hydroxy or lower alkyl group; Y means N or CH.

The compounds according to formula I may be prepared in accordance with the following reaction sequences.

The intermediates according to formula II

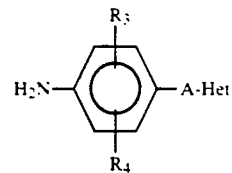

wherein $R_3$, $R_4$, A and Het are the same as defined before, may be prepared according to the methods known in the literature, for example in European patent application No. 52442, in U.S. Pat. No. 4,656,170 and in J. Med. Chem., 17, 273-281 (1974).

The new intermediates of formula IIb

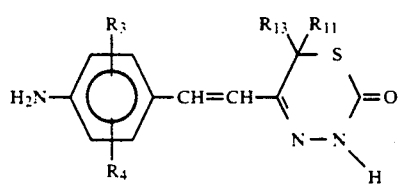

wherein $R_3$, $R_4$, $R_{11}$ and $R_{13}$ are the same as defined before, may be prepared by reacting the compound of formula IIc (J. Org. Chem., 28, 2446-2447, 1963, Hudson, R. et al.)

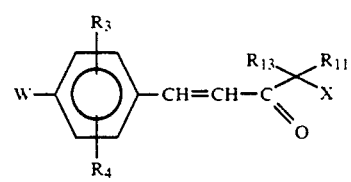

wherein $R_3$, $R_4$, $R_{11}$, $R_{13}$ are the same as defined before, W is nitro or acetamido group and X is halogen, with the compound of formula IId (J. Liebigs Ann. Chem. 791-799, 1977, Ege, G. et al.)

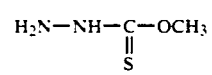

in an inert solvent at elevated temperature to form compounds according to formula IIe

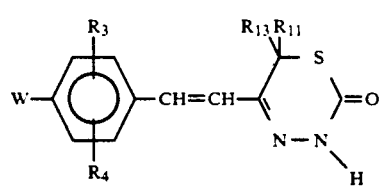

wherein $R_3$, $R_4$, $R_{11}$, $R_{13}$ and W are the same as defined before, after which the nitro group is reduced or the acetamido group is hydrolyzed to form compounds IIb, where $R_3$, $R_4$, $R_{11}$ and $R_{13}$ are the same as defined before.

Compounds of formula IIb may be used in the preparation of compounds according to formula I having the structure Ib

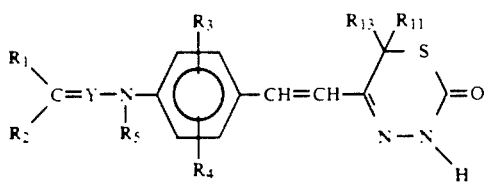

wherein $R_1$, $R_2$, $R_3$, $R_4$, $R_5$, $R_{11}$, $R_{13}$ and Y are as defined before.

A compound of formula II is treated with nitrous acid to form the diazonium compound having formula III

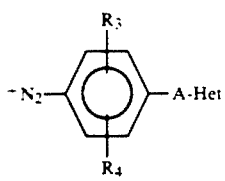

wherein $R_3$, $R_4$, A and Het are the same as defined before. The diazonium compound III is then allowed to react with a compound having an activated methylene group of formula IV

wherein $R_1$ and $R_2$ are the same as defined before, in acidic conditions at a low temperature, preferably about 0° to less than 20° C., more preferably about 0° to about 5° C., to give compounds according to formula I in accordance with the present invention.

Alternatively the compounds I according to the present invention may be prepared by condensation of a compound having formula V

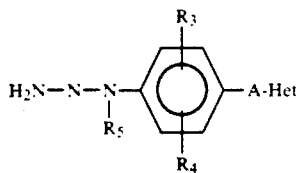

wherein $R_3$, $R_4$, $R_5$, A and Het are the same as defined before, with a compound having formula VI

wherein $R_1$ and $R_2$ are the same as defined before, in an inert solvent at ambient or elevated temperature, preferably about 20° to about 150° C., more preferably about 80 to about 100° C., to give the compounds in accordance with formula I according to the present invention.

Compound V may be prepared from compound III according to the methods known in the literature (FI patent application 863564 or European patent application No. 223937).

Alternatively compounds I according to the present invention where Y is CH may be prepared by allowing compounds II to react with a compound having formula VII

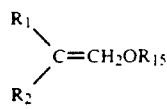

where $R_1$ and $R_2$ are the same as defined before and $R_{15}$ is a lower alkyl group in an inert solvent at normal or elevated temperature to give the compounds in accordance with formula I according to the present invention.

Compounds IV and VI are either commercially available products or may be prepared according to the methods known in the literature.

The compounds of formula I according to the present invention where $R_5$ is lower alkyl group may also be prepared by alkylation of the compounds I, where $R_5$ is hydrogen, with alkylhalide in an inert solvent and in the presence of an inorganic or organic base. Typical inert solvents include lower aliphatic alcohols, lower aliphatic enters, acetic acid and the like.

The term "alkyl" as employed herein by itself or as part of another group includes both straight and branched chain radicals of up to 18 carbon atoms, preferably 1 to 8 carbon atoms, most preferably 1 to 4 carbon atoms, The term "lower alkyl" as employed herein by itself or as part of another group includes both straight and branched chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, hexyl, octyl, decyl and dodecyl including the various branched chain isomers thereof.

The term "acyl" as employed herein by itself or as part of another group refers to an alkylcarbonyl or alkenylcarbonyl group, the alkly and alkenyl groups being defined above.

The term "aryl" as used herein by itself or as part of another group refers to a monocyclic or bicyclic group containing from 6 to 10 carbon atoms in the ring portion. Specific examples for aryl groups are phenyl, naphtyl and the like. "Aroyl" means in a corresponding way an arylcarbonyl group.

The term "alkoxy" as employed herein by itself or as part of another group includes an alkyl group as defined above linked to an oxygen atom.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkenoylamino, arylcarbonylamideo, nitro, cyano, thiol, or alkylthio substituents.

The "substituted" groups may contain 1 to 3, preferably 1 or 2, most preferably 1 of the above mentioned substituents.

Salts of the compounds, when applicable, may be prepared by known methods. Physiologically acceptable salts are useful as active medicaments; however, preferred are the salts with alkali or alkaline earth metals.

The compounds according to the invention are formulated into dosage forms using the principles which are known to a person having average skills in the art. The compounds according to this invention are given to mammalian organisms, i.e., humans, a patient as such or in combination with suitable pharmaceutical excipients in the form of tablets, dragees, capsules, suppositories, emulsions, suspensions or solutions whereby the contents of the active compound is in the formulation from about 1 to 100% per weight. Choosing suitable ingredients for the formula is a routine for those of ordinary skill in the art. It is evident that suitable carriers, solvents gel forming ingredients, dispersion forming ingredients, antioxidants, colours, sweeteners, wetting compounds and other ingredients normally used in this field of technology may be also used.

The compositions are given enterally or parenterally, the oral way being the easiest and preferred way.

The compositions are formulated depending upon the purpose of the medicine, normal uncoated tablets being quite satisfactory. Sometimes it is advisable to use coated tablets, i.e. so-called enterotablets, to secure that the medicine reaches the desired part of the gastrointestinal tract. Dragees and capsules may be used too.

In a conventional way it is possible to make formulations which liberate the active ingredient slowly during a prolonged period of time.

It is also possible to give the desired dose of the medicine using suppositories. Suppositories are also given when the desired systemic effect is desired with patients having nausea and the like symptoms.

The present compounds may be given alone or in a combination with other medicines.

Congestive heart failure is characterized by the decrease in cardiac output and by the increase in right and left ventricular filling pressure. These hermodynamic conditions can produce symptoms of dyspnea, fatigue and edema.

Treatment of congestive heart failure usually focuses on the three principle factors determining cardiac performance: preload, impedance (afterload) and contractility. Vasodilation can improve cardiac function by reducing preload and/or afterload. Cardiac output can be increased directly by augmenting contractility.

The severity of congestive heart failure is usually classified by the New York Heart Association categories; Class I, II, III or IV. The therapeutic benefits of decreases in preload and afterload or increases in contractility may vary among both classes and individual patients. Therefore, it may be advantageous to have compounds which produce varying degrees of vasodilation and increase in contractility.

At the moment a series of compounds the mechanism of which is based on the phosphodiesterase isozyme III ($PDE_{III}$) inhibition are in clinical trials for the treatment of congestive heart failure. These compounds increase the contractility of the cardiac muscle and produce vasodilatation. However, it is possible that the long-term application of those compounds leads to calcium overload in the cardiac muscle, which could trigger arrhythmias. The vasodilation based on the $PDE_{III}$ inhibition is an advantage and thus it was desired also that the present compounds would be $PDE_{III}$ inhibitors. Nevertheless, the main mechanism to increase cardiac contractility should be a mechanism which does not produce calcium overload. The enhancement of the turnover of intracellular calcium released from sarcoplasmic reticulum and the increase of calcium sensitivity of contractile proteins are such mechanisms which do not induce calcium overload.

The contraction in cardiac muscle and in vascular smooth muscle is triggered by the binding of calcium to troponin and to calmodulin, respectively. In order to get increase of cardiac muscle contration and to avoid vasocontraction troponin has been chosen as a target of the present compounds. Thus the main screening method was the measurement of retention times of the compound in troponin high-performance liquid affinity chromatography (HPLAC) column using mobile phase without calcium (EDTA solution in table 1) or with 30 mM calcium ($Ca^{2+}$ solution in table 1) to find out the calcium dependent binding to troponin. Commercially available troponin was coupled to the matrix of SelectiSpher-10™ Activated Tresyl silica HPLAC column (size 10 cm × 5 mm). The compounds were run through the column with the flow rate 1 ml/min and detected by UV-spectrophotometrically.

The $PDE_{III}$ inhibition was studied by using enzyme preparation isolated from dog and guinea-pig heart according to Alajoutsijärvi and Nissinen (Anal. Biochem. 165, 128–132, 1987). The results of the studies are presented in Table 2.

The cardiotonic action of the compound was studied in isolated, electrically driven, right ventricular papillary muscle of guinea-pig. In order to compare the cardiotonic action based on $PDE_{III}$ inhibition to that based on the other mechanisms the experiments were carried out in normal Tyrode's bathing solution (Otani et al., Japan. J. Pharmacol. 45, 425, 1987) and also in the solution with carbachol to eliminate the cardiotonic action due to the $PDE_{III}$ inhibition (Alousi & Johnson, Circulation, 73 (suppl. III), 10–23, 1986). In some of the experiments the extracellular calcium was removed to demonstrate that the present compounds do not function by changing the calcium entry into the cell and that the site of action of the compounds is really located inside the cell and not on the cell membrane (Table 3). The same was verified by using calcium entry blocker verapamil in the bathing solution. The results show that the compounds according to the invention have significant calcium dependent binding to troponin compared to the reference compounds (Table 1). The existence of the mechanism which is independent on the extracellular calcium was confirmed by investigating the ability of the compounds to induce tonic contraction in guinea-pig papillary muscle in the absence of extracellular calcium. In order to confirm that this intracellular mechanism is not related to the $PDE_{III}$ inhibition carbachol was tested to shift the dose-response curves of the compounds. The present compounds have at least one cardiotonic mechanism of action which is not related to the inhibition of $PDE_{III}$ enzyme, because the dose-response curves of some compounds were not shifted to the right in the presence of carbachol (Table 3). The ability of the present compounds to induce a tonic contraction in the absence of extracellular calcium (Table 3) shows that the PDE-independent mechanism is the enhancement of the turnover of calcium released from sarcoplasmic reticulum and/or the increase of calcium sensitivity of contractile proteins. Additionally, the present compounds are also more potent $PDE_{III}$ inhibitors in dog and guinea-pig heart muscle than the reference compounds (Table 2).

TABLE 1
RETENTION TIMES OF THE COMPOUNDS IN TROPONIN-HPLAC COLUMN

| Compound of | Ca$^{2+}$ solution | EDTA solution | Ratio Ca$^{2+}$/EDTA |
|---|---|---|---|
| Example 6 | 4.8 min | 2.7 min | 1.78 |
| Example 1 | 3.5 min | 2.2 min | 1.59 |
| Example 7 | 5.4 min | 4.2 min | 1.29 |
| Example 33 | 6.6 min | 3.9 min | 1.69 |
| Example 41 | 10.5 min | 4.8 min | 2.19 |
| Example 43 | 2.4 min | 1.2 min | 2.00 |
| Example 45 | 2.1 min | 0.9 min | 2.33 |
| Example 49 | 18.4 min | 8.0 min | 2.30 |
| milrinone | 1.2 min | 1.2 min | 1.00 |
| adibendan | 14.8 min | 15.0 min | 0.99 |
| pimobendan | 70.4 min | 79.6 min | 0.88 |
| MCI-154 | 6.4 min | 12.4 min | 0.52 |

TABLE 2
INHIBITION OF CARDIAC PHOSPHODIESTERASE III

| Compound of | IC$_{50}$-value (μM) Dog | IC$_{50}$-value (μM) Guinea-pig |
|---|---|---|
| Example 6 | 0.062 | |
| Example 7 | 0.23 | |
| Example 1 | 0.27 | |
| Example 33 | | 0.006 |
| Example 41 | | 0.024 |
| Example 43 | | 0.017 |
| Example 49 | | 0.024 |
| Example 44 | | 0.051 |
| MCI-154 | 0.42 | |
| milrinone | 0.58 | 0.44 |
| adibendan | 1.00 | |
| pimobendan | 1.75 | |

TABLE 3
CARDIOTONIC EFFECTS OF COMPOUNDS IN GUINEA-PIG PAPILLARY MUSCLE

| Compound of | A EC$_{50}$ μM | B EC$_{50}$ μM | Ratio B/A | C |
|---|---|---|---|---|
| Example 6 | 0.17 | 0.16 | 0.94 | yes |
| Example 7 | 0.74 | 2.7 | 3.6 | * |
| Example 1 | 1.8 | 3.6 | 2.0 | yes |
| Example 33 | 0.30 | | | yes |
| Example 41 | 0.12 | | | yes |
| Example 44 | 1.1 | | | yes |
| Example 49 | 1.1 | | | yes |
| milrinone | 0.36 | 5.5 | 15.3 | no |
| pimobendan | 3.3 | | | no |

A = experiments carried out without carbachol
B = experiments carried out in the presence of 10 μM carbachol
C = ability to induce tonic contraction in the absence of extracellular calcium; drug concentration 100 μM
*precipitation occurs at 100 μM concentration The invention is illustrated but not limited by following Examples:

EXAMPLE 1

6-[4-(1,1-dicyanomethylidenehydrazino)phenyl]-4,5-dihydropyridazin-3(2H)one

To a solution containing 0.95 g of 6-(4-aminophenyl)-4,5-dihydropyridazin-3(2H)one and 2.5 ml of concentrated hydrochloric acid in 37.5 ml of water 0.38 g of sodium nitrite in 2.5 ml of water was added while stirring and cooling (0-5° C.). After 10 min 0.33 g of malononitrile in 2.5 ml of water was added. The solution was stirred for 1.5 h at room temperature after which the pH was adjusted to 6.0 with sodium acetate solution. The product was filtered, washed with water and ethanol. Yield 1.25 g, mp 283° C.

$^1$H NMR (DMSO-d$_6$) δ:

2.52 (m, 2H), 2.94 (m, 2H), 7.48 (d, 2H, J = 9 Hz), 7.80 (d, 2H, J = 9 Hz), 10.90 (s, 1H), 13.0 (br s, 1H).

EXAMPLE 2

6-[4-(1,1-dicyanomethylidenehydrazino)phenyl]pyridazin-3(2H)one 0.36 g of 6-(4-aminophenyl)pyridazin-3(2H)one was treated with sodium nitrite and malononitrile as described in Example 1. Yield 0.45 g, mp > 300° C.

$^1$H NMR (DMSO-d$_6$) δ:

7.00 (d, 1H, J = 10 Hz), 7.53 (d, 2H, J = 9 Hz), 7.90 (d, 2H, J = 9 Hz), 8.04 (d, 1H, J = 10 Hz), 12.9 (br s, 1H), 13.20 (s, 1H).

EXAMPLE 3

6-[4-(1-cyano-1-ethoxycarbonylmethylidenehydrazino)phenyl]-4,5-dihydropyridazin-3(2H)one 0.37 g of 6-(4-aminophenyl)-4,5-dihydropyridazin-3(2H)one was treated with sodium nitrite and ethyl cyanoacetate as described in Example 1. Yield 0.5 g, mp 235°-239° C.

$^1$M NMR (DMSO-d$_6$) δ:

1.30 (t, 3H, J = 8 Hz), 2.43 (m, 2H), 2.94 (m, 2H), 4.30 (q, 2H, J = 8 Hz), 7.52 (d, 2H, J = 9 Hz), 7.80 (d, 2H, J = 9 Hz), 10.92 (s, 1H), 12.35 (s, 1H).

EXAMPLE 4

6-[4-(1,1-dicyanomethylidenehydrazino)-2-hydroxyphenyl]-4,5-dihydropyridazin-3(2H)one 0.4 g of 6-(4-amino-2-hydroxyphenyl)-4,5-dihydropyridazin-3(2H)one was treated with sodium nitrite and malononitrile as described in Example 1. Yield 0.2 g, mp 168°-171° C.

$^1$H NMR (DMSO-d$_6$) δ:

2.58 (m, 2H), 3.27 (m, 2H), 6.93 (m, 2H), 7.94 (d, 1H), 10.2 (br s, 1H), 11.98 (s, 1H), 12.5 (br s, 1H).

EXAMPLE 5

6-[4-(1-cyano-1-(N,N-diethylaminocarbonyl)methylidenehydrazino)phenyl]-4,5-dihydropyridazin-3(2 1 H)one 0.5 g of 6-(4-aminophenyl)-4,5-dihydropyridazin-3(2H)one was treated with sodium nitride and N,N-diethylcyanoacetamide. Yield 0.29 g, mp 200°-205° C.

$^1$H NMR (DMSO-d$_6$) δ:

1.00-1.45 (2×t, 2×3H), 2.40 (m, 2H), 2.90 (m, 2H), 7.40 (m, 2H), 7.75 (m, 2H), 10.80 (s, 1H), 11.45 (s, 1H).

EXAMPLE 6

6-[4-(1,1-dicyanomethylidenehydrazino)phenyl]-4,5-dihydro-5-methylpyridazin-3(2H)one 0.2 g of 6-(4-aminophenyl)-5-methyl-4,5-dihydropyridazin-3(2H)one was treated with sodium nitrite and malononitrile as described in Example 1. Yield 0.25 g, mp 258°-263° C.

$^1$H NMR (DMSO-d$_6$) δL:

1.08 (d, 3H, J = 7 Hz), 2.12-2.85 (m, 2H), 3.39 (m, 1H), 7.48 (d, 2H, J = 9 Hz), 7.85 (d, 2H, J = 9 Hz), 10.98 (s, 1H), 13.0 (br s, 1H).

EXAMPLE 7

6-[4-(1,1-diacetylmethylidenehydrazino)phenyl]-4,5-dihydropyridazin-3(2H)one 0.45 g of 6-(4-aminophenyl)-4,5-dihydropyridazin-3(2H)one was treated with sodium nitrite and 2,4-pentanedione as described in Example 1. Yield 0.7 g, mp 218°–223° C.

$^1$H NMR (DMSO-$d_6$) δ:
2.43 (s, 6H), 2.48 (m, 2H), 2.92 (m, 2H),
7.60 (d, 2H, J = 9 Hz), 7.82 (d, 2H, J = 9 Hz), 10.95 (s, 1H),
13.90 (s, 1H).

EXAMPLE 8

6-[4-(1-ethoxycarbonyl-1-nitromethylidenehydrazino)-phenyl]-4,5-dihydropyridazin-3(2H)one 0.57 g of 6-(4-aminophenyl)-4,5-dihydropyridazin-3(2H)one was treated with sodium nitrite and ethyl nitroacetate as described in Example 1. Yield 0.90 g, mp 237°–241° C.

$^1$H NMR (DMSO-$d_6$) δ:
1.32 (t, 3H), 2.45 (t, 2H), 2.96 (t, 2H), 4.39 (q, 2H),
7.54 (m, 2H), 7.83 (m, 2H), 10.89 (s, 1H), 12.00 (s, 1H).

EXAMPLE 9

6-[4-(1-acetyl-1-(N,N-diethylaminocarbonyl)methylidene-hydrazino)phenyl]-4,5-dihydropyridazin-3(2H)one 0.5 g of 6-(4-aminophenyl)-4,5-dihydropyridazin-3(2H)one was treated with sodium nitrite and N,N-diethylacetoacetamide. Yield 0.26 g, mp 257°–262° C.

$^1$H NMR (DMSO-$d_6$) δ:
1.00 (t, 3H), 1.15 (t, 3M), 2.45 (s, 3H), 2.50 (m, 2H),
3.00 (2×m, 2×2H), 3.50 (m, 2H), 7.45 (m, 2H),
7.75 (m, 2H), 10.85 (s, 1H), 13.00 (br s, 1H).

EXAMPLE 10

6-[4-(1-ethoxycarbonyl-1-(4-pyridyl)methylidenehydrazino)-phenyl]-4,5-dihydropyridazin-3(2H)one 0.57 g of 6-(4-aminophenyl)-4,5-dihydropyridazin-3(2H)one was treated with sodium nitrite and ethyl 4-pyridyl acetate. Yield 0.67 g, mp 225°–230° C.

$^1$H NMR (DMSO-$d_6$) δ:
1.33 (t, 3H), 2.44 (t, 2H), 2.94 (t, 2H), 4.40 (q, 2H),
7.45 (m, 2H), 7.70 (m, 2H), 7.74 (m, 2H), 8.60 (m, 2H),
10.89 (s, 1H), 12.17 (s, 1H).

EXAMPLE 11

6-[4-(1,1-bis(ethoxycarbonyl)methylidenehydrazino)-phenyl]-4,5-dihydropyridazin-3(2H)one 0.38 g of 6-(4-aminophenyl)-4,5-dihydropyridazin-3(2H)one was treated with sodium nitrite and diethyl malonate as described in Example 1. Yield 0.4 g, mp 175°–178° C.

$^1$H NMR (DMSO-$d_6$) δ:
1.25 (t, 3H, J = 8 Hz), 1.27 (t, 3H, J = 8 Hz), 2.48 (m, 2H),
2.92 (m, 2H), 4.24 (q, 2H, J = 8 Hz), 4.32 (q, 2H, J = 8 Hz), 7.40 (d, 2H, J = 9 Hz), 7.75 (d, 2H, J = 9 Hz),
10.82 (s, 1H), 11.96 (s, 1H).

EXAMPLE 12

6-[4-(1-acetyl-1-ethoxycarbonyl)methylidenehydrazino)phenyl]-4,5-dihydropyridazin-3(2H)one 0.5 g of 6-(4-aminophenyl)-4,5-dihydropyridazin-3(2H)one was treated with sodium nitrite and ethyl acetoacetate as described in Example 1. Yield 0.34 g, mp 110°–115° C.

$^1$H NMR (DMSO-$d_6$) δ:
1.30 (t, 3H), 2.45 (s, 3H), 2.50 (m, 2H), 2.90 (m, 2H),
4.30 (m, 2H), 7.50 (m, 2H), 7.80 (m, 2H), 11.05 (s, 1H),
11.85 (br s, 1H).

EXAMPLE 13

6-[4-(2,6-dioxo-1-cyclohexylidenehydrazino)phenyl]-4,5-dihydropyridazin-3(2H)one 0.38 g of 6-(4-aminophenyl)-4,5-dihydropyridazin-3(2H)one was treated with sodium nitrite and 1,3-cyclohexanedione as described in Example 1. Yield 0.6 g, mp 253°–256° C.

$^1$H NMR (DMSO-$d_6$) δ:
1.96 (m, 2H), 2.30–3.10 (m, 8H), 7.64 (d, 2H, J = 9 Hz),
7.84 (d, 2H, J = 9 Hz), 10.90 (s, 1H), 14.85 (s, 1H).

EXAMPLE 14

6-[4-(3,5-dimethyl(4-pyrazolidenehydrazino)phenyl]-4,5-dihydropyridazin-3(2H)one 0.38 g of 6-(4-aminophenyl)-4,5-dihydropyridazin-3(2H)one was treated with sodium nitrite and 3,5-dimethylpyrazole as described in Example 1. Yield 0.4 g, mp 315°–318° C.

$^1$H NMR (DMSO-$d_6$) δ:
2.42 (s, 6H), 2.46 (m, 2H), 3.03 (m, 2H),
7.78 (d, 2H, J = 9 Hz), 7.87 (d, 2H, J = 9 Hz), 10.97 (s, 1H),
12.85 (s, 1H).

EXAMPLE 15

6-[4-(1,1-bis(ethoxycarbonyl)methylidenehydrazino)-phenyl]-4,5-dihydropyridazin-3(2H)one A solution containing 0.60 g 6-(4-hydrazinophenyl)-4,5-dihydropyridazin-3(2H)one hydrochloride and 0.45 g of diethyl ketomalonate in 10 ml of 50% ethanol was stirred for 3 h at room temperature. Water was added and the product was filtered and washed with water. Yield 0.35 g, mp 176°–178° C.

$^1$H NMR (DMSO-$d_6$) δ:
1.25 (t, 3H, J = 8 Hz), 1.27 (t, 3H, J = 8 Hz), 2.48 (m, 2H),
2.92 (m, 2H), 4.24 (q, 2H, J = 8 Hz), 4.32 (q, 2H, J = 8 Hz),
7.40 (d, 2H, J = 9 Hz), 7.75 (d, 2H, J = 9 Hz), 10.82 (s, 1H),
11.96 (s, 1H).

EXAMPLE 16

6-[4-(1-acetyl-1-phenylmethylidenehydrazino)phenyl]-4,5-dihydropyridazin-3(2H)one 0.5 g of 6-(4-aminophenyl)4,5-dihydropyridazin-3(2H)one was treated with sodium nitrite and 3-phenyl-2-butanone as described in Example 1. Yield 0.12 g, mp 113°–118° C.

$^1$H NMR (DMSO-$d_6$) δ:
2.50 (s, 3H), 2.50 (m, 2H), 2.90 (m, 2H), 7.10–7.60 (m, 5H),
7.40 (m, 2H), 7.70 (m, 2H), 10.05 (s, 1H), 10.75 (s, 1H).

EXAMPLE 17

6-[4-(1-chloro-1-ethoxycarbonyl)methylidenehydrazino)phenyl]-4,5-dihydropyridazin-3(2H)one 0.38 g of 6-(4-aminophenyl)-4,5-dihydropyridazin-3(2H)one was treated with sodium nitrite and ethyl 2-chloroacetoacetate as decribed in Example 1. Yield 0.45 g, mp 225° C.

$^1$H NMR (DMSO-d$_6$) δ:
1.30 (t, 3H, J= 7 Hz), 2.42 (m, 2H), 2.93 (m, 2H),
4.30 (g, 2H, J= 7 Hz), 7.42 (d, 2H, J= 9 Hz),
7.75 (d, 2H, J= 9 Hz), 10.68 (s, 1H), 10.82 (s, 1H).

EXAMPLE 18

6-[4-(1-carboxamido-1-cyanomethylidenehydrazino)-phenyl]-4,5-dihydropyridazin-3(2H)one 0.57 g of 6-(4-aminophenyl)-4,5-dihydropyridazin-3(2H)one was treated with sodium nitrite and cyanoacetamide as described in Example 1. Yield 0.79 g, mp > 350° C.

$^1$H NMR (DMSO-d$_6$) δ:
2.50 (t, 2H), 2.94 (t, 2H), 7.76 (m, 4H), 10.96 (s, 1H), 11.42 (d, 2H), 14.22 (s, 1'H).

EXAMPLE 19

6-[4-(1acetyl-1-benzoylmethylidenehydrazino)phenyl]-4,5-dihydropyridazin-3(2H)one 0.57 g of 6-(4-aminophenyl)-4,5-dihydropyridazin-3(2H)one was treated with sodium nitrite and 4-phenyl-2,4-butanedione. Yield 0.29 g, mp 195°-198° C.

$^1$H NMR (DMSO-d$_6$) δ:
2.48 (t, 2H), 2.51 (s, 3H), 2.92 (t, 2H), 7.41 (m, 2H),
7.64 (m, 2H), 7.66 (m, 5H), 10.89 (s, 1H), 11.31 (s, 1H).

EXAMPLE 20

6-[4-(1-cyano-1-(2-pyridyl)methylidenehydrazino)-phenyl]-4,5-dihydropyridazin-3(2H)one 0.57 g of 6-(4-aminophenyl)-4,5-dihydropyridazin-3(2H)one was treated with sodium nitrite and 4-pyridylacetonitrile. Yield 0.83 g, mp 279°-283° C.

$^1$H NMR (DMSO-d$_6$) δ:
2.48 (t, 2H), 2.92 (t, 2H), 7.42 (m, 1H), 7.52 (m, 2H),
7.78 (m, 2H), 7.80 (m, 1H), 7.99 (m, 1H), 8.71 (m, 1H),
10.88 (s, 1H), 11.62 (s, 1H).

EXAMPLE 21

6-[4-(1,1-diacetylmethylidenehydrazino)phenyl]-4,5-dihydro-5-methylpyridazin-3(2H)one 0.4 g of 6-(4-aminophenyl)-5-methyl-4,5-dihydropyridazin-3(2H)one was treated with sodium nitrite and 2,4-pentanedione as described in Example 1. Yield 0.6 g, mp 194°-196° C.

$^1$H NMR (DMSO-d$_6$) δ:
1.08 (d, 2H, J= 7 Hz), 2.10-2.85 (m, 2H), 3.40 (m, 1H),
7.63 (d, 2H, J= 9 Hz), 7.86 (d, 2H, J= 9 Hz), 10.90 (s, 1H),
13.88 (s, 1H).

EXAMPLE 22

6-[4-(1-amino-1-carboxamidomethylidenehydrazino)-phenyl]-4,5-dihydropyridazin-3(2H)one The compound prepared in Example 17 was dissolved in conc. ammonia and stirred for 5 hours at room temperature. The product was filtered, washed with water and dried. Mp 260°-266° C.

$^1$H NMR (DMSO-d$_6$) δ:
2.39 (m, 2H), 2.87 (m, 2H), 5.93 (s, 2H),
7.10 (d, 2H, J=9 Hz), 7.15 (s, 1H), 7.50 (s, 1H).
7.56 (d, 2H, J= 9 Hz), 8.68 (s, 1H), 10.66 (s, 1H).

EXAMPLE 23

6-[4-(2,2-bis(ethoxycarbonyl)vinyl)aminophenyl]-4,5-dihydropyridazin-3(2H)one

A solution containing 0.38 g of 6-(4-aminophenyl)-4,5-dihydropyridazin-3(2H)one and 0.45 g of diethyl ethoxymethylenemalonate in 5 ml of dry ethanol was refluxed for 1.5 h. After cooling the product was filtered and washed with ethanol. Yield 0.3 g, mp 164° C.

$^1$H NMR (DMSO-d$_6$) δ:
1.25 (t, 6H, J= 7 Hz), 2.43 (m, 2H), 2.94 (m, 2H),
4.17 (q, 4H, J= 7 Hz), 7.42 (d, 2H, J= 9 Hz),
7.76 (d, 2H, J= 9 Hz), 8.42 (s, 1H), 10.70 (s, 1H),
10.88 (s, 1H).

EXAMPLE 24

6-[4-(2,2-dicyanovinyl)aminophenyl]-4,5-dihydropyridazin-3(2H)one

A solution containing 0.38 g of 6-(4-aminophenyl)-4,5-dihydropyridazin-3(2H)one and 0.3 g of ethoxymethylenemalononitrile in 5 ml of ethanol was refluxed for 1 h. Yield 0.25 g, mp 290°-295° C.

$^1$H NMR (DMSO-d$_6$) δ:
2.48 (m, 2H), 2.94 (m, 2H), 7.50 (d, 2H, J= 9 Hz),
7.73 (d, 2H, J= 9 Hz), 8.58 (s, 1H), 10.88 (s, 1H),
11.20 (s, 1H).

EXAMPLE 25

6-[4-(2,2-diacetylvinyl)aminophenyl]-4,5-dihydropyridazin-3(2H)one

A solution containing 0.38 g of 6-(4-aminophenyl)-4,5-dihydropyridazin-3(2H)one and 0.4 g of 3-ethoxymethylene-2,4-pentanedione in 5 ml of ethanol was refluxed for 1 h. Yield 0.3 g, mp 218°-222° C.

$^1$H NMR (DMSO-d$_6$) δ:
2.37 (s, 6H), 2.44 (m, 2H), 2.96 (m, 2H),
7.55 (d, 2H, J= 9 Hz), 7.80 (d, 2H, J= 9 Hz),
8.47 (d, 1H, J= 13 Hz), 10.90 (s, 1H),
12.52 (d, 1H, J= 13 Hz).

EXAMPLE 26

6-[4-(1-ethoxycarbonyl-1-ethoxycarbonyl(acetyl)methylidenehydrazino)phenyl]-4,5-dihydropyridazin-3(2H)one 0.37 g of 6-(4-aminophenyl)-4,5-dihydropyridazin-3(2H)one was treated with sodium nitrite and 0.43 g of diethyl 3-ketoglutarate as described in Example 1. Yield 0.75 g, mp 174°-181° C.

$^1$H NMR (DMSO-d$_6$) δ:
1.17 (t, 3H, J= 7 Hz), 1.29 (t, 3H, J= 7 Hz), 2.45 (m, 2H),
2.93 (m, 2H), 3.87 (s, 2H), 4.09 (q, 2H, J= 7 Hz),
4.32 (q, 2H, J= 7 Hz), 7.53 (d, 2H, J= 9 Hz),
7.78 (d, 2H, J= 9 Hz), 10.85 (s, 1H), 11.93 (s, 1H).

EXAMPLE 27

6-[4-(1,1-dicyanomethylidene-N-methyl(hydrazino))-phenyl]-4,5-dihydropyridazin-3(2H)one A solution containing 0.28 g of the compound described in Example 1, 0.16 ml of methyl iodide and 0.2 g of potassium carbonate was refluxed for 6 hours. The solvent was evaporated and ethanol followed with water were added. Mp 247°–250° C.

$^1$H NMR (DMSO-$d_6$) δ:
2.44 (m, 2H), 2.95 (m, 2H), 4.07 (s, 3H),
7.56 (d, 2H, J= 9 Hz), 7.82 (d, 2H, J= 9 Hz), 10.94 (s, 1H).

EXAMPLE 28

6-[4-(2-amino-1,1,3-tricyanopropenylidene)hydrazinophenyl]-4,5-dihydropyridazin-3(2H)one 0.37 g of 6-(4-aminophenyl)-4,5-dihydropyridazin-3(2H)one was treated with sodium nitrite and 0.28 g of 2-amino-1-propenyl-1,1,3-tricarbonitrile as described in Example 1. Yield 85%, mp > 300° C.

$^1$H NMR (DMSO-$d_6$) δ:
2.48 (m, 2H), 2.94 (m, 2H), 7.63 (d, 2H, J= 9 Hz),
7.71 (d, 2H, J= 9 Hz), 9.98 (br s, 2H), 10.84 (s, 1H), 11.09 (s, 1H).

EXAMPLE 29

6-[4-(1,1-dicyanomethylidene-N''-methyl(hydrazino))-phenyl]-4,5-dihydro-5-methylpyridazin-3(2H)one A solution containing 0.28 g of the compound described in Example 6, 0.16 ml of methyl iodide and 0.2 g of potassium carbonate was refluxed for 6 hours. The solvent was evaporated and 2 ml of ethanol followed by 5 ml of water were added. The product was filtered and dried. Yield 0.2 g, mp 161°–165° C.

$^1$H NMR (DMSO-$d_6$) δ:
1.07 (d, 3H, J= 7 Hz), 2.12–2.86 (m, 2H), 3.40 (m, 1H),
4.07 (s, 3H), 7.55 (d, 2H, J= 9 Hz), 7.84 (d, 2H, J= 9 Hz),
11.00 (s, 1H).

EXAMPLE 30

6-[4-(2-amino-1,3-dicyano-3-methoxycarbonyl-propenylidene)-hydrazinophenyl]-4,5-dihydropyridazin-3(2H)one 0.37 g of 6-(4-aminophenyl)-4,5-dihydropyridazin-3(2H) one was treated with sodium nitrite and 0.35 g of methyl 3-amino-2,4-dicyanocrotonate as described in Example 1. Yield 0.5 g, mp >300° C.

$^1$H NMR (DMSO-$d_6$) δ:
2.42 (m, 2H), 2.94 (m, 2H), 3.71 (s, 3H),
7.63 (d, 2H, J= 9 Hz), 7.78 (d, 2H, J= 9 Hz),
8.80 (br s, 1H), 9.10 (br s, 1H), 10.86 (s, 1H),
12.23 (br s, 1H).

EXAMPLE 31

6-[4-(1,1-dicyanomethylidenehydrazino)phenyl]-4,5-dihydro-4methylpyridazin-3(2H)one 0.44 g of 6-(4-aminophenyl)-4,5-dihydro-4-methyl-pyridazin-3(2H)one was treated with sodium nitrite and malononitrile as described in Example 1. Yield 0.3 g, mp 240°–245° C.

$^1$H NMR (DMSO-$d_6$) δ:
1.15 (d, 3H), 2.65 (s, 1H), 3.10 (m, 2H), 7.50 (m, 2H), 7.85 (m, 2H), 10.90 (s, 1H), 11.00 (br s, 1H).

EXAMPLE 32

2-[4-(1,1-dicyanomethylidenehydrazino)phenyl]-5,6-dihydro-1,3,4-oxadiazin-5(4H)one 0.76 g of 2-(4-aminophenyl)-5,6-dihydro-1,3,4-oxadiazin-5-(4H)one was treated with sodium nitrite and malononitrile as described in Example 1. Yield 0.65 g, mp 350° C. (decomp.).

$^1$H NMR (DMSO-$d_6$) δ:
4.75 (s, 2H), 7.50 (m, 2H), 7.81 (m, 2H), 11.00 (s, 1H), 12–14 (b, 1H).

EXAMPLE 33

(E)-6-[2-(4-(1,1-dicyanomethylidenehydrazino)phenyl)-ethenyl]-4,5-dihydro-5-methylpyridazin-3(2H)one 0.23 g of 6-[2-(4-aminophenyl)ethenyl]-4,5-dihydro-5-methylpyridazin-3(2H)one was treated with sodium nitrite and malononitrile as described in Example 1. Yield 0.3 g, mp 195°–200° C.

$^1$H NMR (DMSO-$d_6$) δ:
1.08 (d, 3H, J= 7 Hz), 2.10–2.78 (m, 2H), 3.36 (m, 1H),
6.81 (d, 1H, J= 17 Hz), 7.03 (d, 1H, J= 17 Hz),
7.47 (d, 2H, J= 9 Hz), 7.64 (d, 2H, J= 9 Hz), 10.90 (s, 1H),
12.80 (br s, 1H).

EXAMPLE 34

(E)-6-[2-(4-(1,1-dicyanomethylidenehydrazino)phenyl)-ethenyl]-5-methylpyridazin-3(2H)one 0.47 g of 6-[2-(4-aminophenyl)ethenyl]-5-methyl-pyridazin-3(2H)one was treated with sodium nitrite and manononitrile as described in Example 1. Yield 0.6 g, mp 325° C. (decomp.).

$^1$H NMR (DMSO-$d_6$) δ:
2.28 (d, 3H, J= 1 Hz), 6.69 (d, 1H, J= 1 Hz),
7.13 (d, 1H, J= 17 Hz), 7.30 (d, 1H, J= 17 Hz),
7.47 (d, 2H, J= 9 Hz), 7.69 (d, 2H, J= 9 Hz),
12.70 (br s, 1H), 12.92 (s, 1H).

EXAMPLE 35

6-[2-4-(1,1-dicyanomethylidenehydrazino)phenyl)ethyl]-4,5-dihydro-5-methylpyridazin-3(2H)one 0.45 g of 6-[2-(4-aminophenyl)ethyl]-4,5-dihydro-5-methylpyridazin-3(2H)one was treated with sodium nitrite and malononitrile as described in Example 1. Yield 0.59 g, 153°–157° C.

$^1$H NMR (DMSO-$d_6$) δ:
1.00 (d, 3H, J= 7 Hz), 2.10–2.95 (m, 7H),
7.27 (d, 2H, J= 9 Hz), 7.38 (d, 2H, J= 9 Hz), 10.44 (s, 1H),
12.90 (br s, 1H).

EXAMPLE 36

6-[2,5-dimethyl-4(1,1-dicyanomethylidenehydrazino)-phenyl]-4,5-dihydro-5-methylpyridazin-3(2H)one 0.46 g of 6-(4-amino-2,5-dimethylphenyl)-4,5-dihydro-5-methylpyridazin-3(2H)one was treated with sodium nitrite and malononitrile as described in Example 1. Yield 0.6 g, mp 197°–199° C.

$^1$H NMR (DMSO-$d_6$) δ:
0.97 (d, 3H, J= 7 Hz), 2.10–3.15 (m, 3H), 2.27 (s, 3H),
2.31 (s, 3H), 7.21 (s, 1H), 7.23 (s, 1H), 10.83 (s, 1H),
12.10 (br s, 1H).

EXAMPLE 37

6-[4-(1,1-dicyanomethylidenehydrazino)phenyl]-5-methylpyridazin-3(2H)one 0.2 g of 6-(4-aminophenyl)-5-methylpyridazin-3(2H)one was treated with sodium nitrite and malononitrile as described in Example 1. Yield 0.2 g, mp 265°–273° C.

¹H NMR (DMSO-d₆) δ:
2.12 (d, 3H, J = 1 Hz), 6.80 (d, 1H, J = 1 Hz), 7.53 (s, 4H),
11.95 (br s, 1H), 13.03 (s, 1H).

EXAMPLE 38

6-[4-(1,1-dicyanomethylidene-N-methylhydrazino)phenyl]-4,5-dihydro-5-methylpyridazin-3(2H)one 0.28 g of 6-[4(1,1-dicyanomethylidenehydrazino)phenyl]-4,5-dihydro-5-methylpyridazin-3(2H)one (Example 6), 0.16 ml of methyl iodide and 0.2 g of potassium carbonate in 10 ml of acetone was refluxed for 6 h. The solvent was evaporated in vacuo and the residue was treated with 50% ethanol-water. The product was filtered, yield 0.2 g, mp 161°–165° C.

¹H NMR (DMSO-d₆) δ:
1.07 (d, 3H, J = 7 Hz), 2.12–2.86 (m, 2H), 3.40 (m, 1H),
4.07 (s, 3H), 7.55 (d, 2H, J = 9 Hz), 7.84 (d, 2H, J = 9 Hz),
11.00 (s, 1H).

EXAMPLE 39

6-[4-(1-cyano-1-carbamidomethylidenehydrazino)phenyl]-4,5-dihydro-5-methylpyridazin-3(2H)one 0.48 g of 6-(4-aminophenyl)-4,5-dihydro-5-methylpyridazin-3(2H)one was treated with sodium nitrite and cyanoacetamide as described in Example 1. Yield 0.66 g, mp 261°–265° C.

¹H NMR (DMSO-d₆) δ:
1.08 (d, 3H, J = 7 Hz), 2.10–2.92 (m, 2H), 3.40 (m, 1H),
7.60 (br d, 2H), 7.72 (s, 4H), 10.90 (s, 1H), 11.78 (s, 1H).

EXAMPLE 40

4-[4-(1,1-dicyanomethylidenehydrazino)phenyl]-phtalazin-1-(2H)one 0.23 g of 4-(4-aminophenyl)phtalazin-1(2H)one was treated with sodium nitrite and malononitrile as described in Example 1. Yield 0.25 g, mp 350° C. (decomp.).

¹H NMR (DMSO-d₆) δ:
7.50–8.10 (m, 8H), 11.80 (s, 1H), 13.00 (br s, 1H).

EXAMPLE 41

5-[4-(1,1-dicyanomethylidenehydrazino)phenyl]-5,6-dihydro-6-methyl-1,3,4-thiadiazin-2(3H)one 0.25 g of 5-(4-aminophenyl)-5,6-dihydro-6-methyl-1,3,4-thiadiazin-2(3H)one was treated with sodium nitrite and malononitrile as described in Example 1. Yield 0.29 g, mp 225°–229° C.

¹H NMR (DMSO-d₆) δ:
2.45 (d, 3H), 4.70 (m, 1H), 7.55 (m, 2H), 7.85 (m, 2H), 11.50 (s, 1H), 13.00 (br s, 1H).

EXAMPLE 42

2-[4-(1,1-dicyanomethylidenehydrazino)phenyl]-5,6-dihydro-1,3,4-triazin-5(4H)one 0.19 g of 2-(4-aminophenyl)-5,6-dihydro-1,3,4-triazin-5(4H)one was treated with sodium nitrite and malononitrile as described in Example 1. Yield 0.24 g, mp > 350° C.

¹H NMR (DMSO-d₆) δ:
3.82 (s, 2H), 7.36 (s, 1H), 7.62 (br s, 1H),
7.50 (d, 2H, J = 9 Hz), 7.78 (d, 2H, J = 9 Hz), 10.40 (s, 1H).

EXAMPLE 43

6-[4-(1,1-dicyanomethylidenehydrazino)phenyl]-4,5-dihydro-5-methyl-1,2,4-triazin-3(2H)one 1.5 g of 6-(4-aminophenyl)-4,5-dihydro-5-methyl-1,2,4-triazin-3(2H)one was treated with sodium nitrite and malononitrile as described in Example 1. Yield 0.9 g, mp > 350° C. (decomp.).

¹H NMR (DMSO-d₆) δ:
1.20 (d, 3H, J = 7.2 Hz), 4.42–4.80 (m, 1H), 7.40 (s, 1H),
7.49 (d, 2H, J = 9 Hz), 7.69 (d, 2H, J = 9 Hz), 9.82 (s, 1H), 11.80 (br s, 1H).

EXAMPLE 44

5-[4-(1,1-dicyanomethylidenehydrazino)phenyl]-5,6-dihydro-1,3,4-thiadiazin-2(3H)one 0.28 g of 5-(4-aminophenyl)-5,6-dihydro-1,3,4-thiadiazin-2(3H)one was treated with sodium nitrite and malononitrile as described in Example 1. Yield 0.21 g, mp 210°–215° C.

¹H NMR (DMSO-d₆) δ:
4.25 (s, 2H), 7.25 (m, 2H), 7.85 (m, 2H), 11.00 (s, 1H), 13.00 (br s, 1H).

EXAMPLE 45

6-[4-(1,1-dicyanomethylidenehydrazino)phenyl]-4,5-dihydro-1,2,4-triazin-3(2H)one 0.3 g of 6-(4-aminophenyl)-4,5-dihydro-1,2,4-triazin-3(2H)one was treated with sodium nitrite and malononitrile as described in Example 1. Yield 0.41 g, mp. > 350° C. (decomp).

¹H NMR (DMSO-d₆) δ:
4.27 (s, 2H), 7.26 (s, 1H), 7.38 (br s, 1H),
7.48 (d, 2H, J = 9 Hz), 7.70 (d, 2H, J = 9 Hz), 9.87 (s, 1H).

EXAMPLE 46

5-[2-(4-nitrophenyl]-5,6-dihydro-1,3,4-thiadiazin-2(3H)one

A solution containing 11.2 g of 1-chloro-4-(4-nitrophenyl)-2-oxo-3-butene (J. Org. Chem. 28, 2446, 1963) and 6.8 g of hydrazinecarbothioic acid O-methylester in 200 ml of acetonitrile was refluxed for 3 h. The crystals were filtered and washed with acetonitrile and ether. Yield 7.7 g (59%), mp. 231°–240° C.

¹H NMR (DMSO-d₆) δ:
4.11 (s, 2H), 7.20 (d, 1H, J = 17 Hz), 7.37 (d, 1H, J = 17 Hz),
7.88 (d, 2H, J = 9 Hz), 8.24 (d, 2H, J = 9 Hz), 11.66 (s, 1H).

EXAMPLE 47

5-[2-(4-aminophenyl)ethenyl]-5,6-dihydro-1,3,4-thiadiazin-2(3H)one

To a solution containing 7.5 g of 5-[2-(4-nitrophenyl)ethenyl]-5,6-dihydro-1,3,4-thiadiazin-2(3H)one (Example 46) in 300 ml of pyridine 18.0 g sodium dithionite in 150 ml of water was gradually added. The mixture was refluxed for 5 h. The organic phase was separated and evaporated to dryness in vacuo. The residue was treated with water and the product was filtered. Yield 4.0 g (60%), mp. 188°–196° C.

¹H NMR (DMSO-d₆) δ:

3.98 (s, 2H), 5.53 (br s, 2H), 6.57 (d, 2H, J= 9 Hz), 6.63 (d, 1H, J= 17 Hz), 7.03 (d, 1H, J= 17 Hz), 7.30 (d, 2H, J= 9 Hz), 11.32 (s, 1H).

EXAMPLE 48

5-[2-(4-acetamidophenyl)ethanyl]-5,6-dihydro-1,3,4-thiadiazin-2(3H)one

A mixture containing 4.0 g of 1-chloro-4-(4-acetamidophenyl)-2-oxo-3-butene (J. Org. Chem., 28, 2446, 1963) and 2.3 g of hydrazinecarbothioic acid O-methylester in 150 ml of toluene was refluxed for 3 h. The crystals were filtered and washed with toluene. Yield 3.0 g (65%), mp. 235°–240° C.

$^1$H NMR (DMSO-d$_6$) δ:
2.05 (s, 3H), 4.04 (s, 2H), 6.85 (d, 1H, J= 17 Hz), 7.14 (d, 1H, J= 17 Hz), 7.50 (d, 2H, J= 9 Hz), 7.61 (d, 2H, J= 9 Hz), 10.06 (s, 1H), 11.47 (s, 1H).

EXAMPLE 49

5-[2-(4-(1,1-dicyanomethylidenehydrazino)phenyl)ethenyl]-5,6-dihydro-1,3,4-thiadiazin-2(3 1 H)one 0.4 g of 5-[2-(4-aminophenyl)ethenyl]-5,6-dihydro-1,3,4-thiadiazin-2(3H)one (Example 47) was treated with sodium nitrite and malononitrile as described in Example 1. Yield 0.34 g, mp.> 350° C. (decomp).

$^1$H NMR (DMSO-d$_6$) δ:
4.04 (s, 2H), 6.93 (d, 1H, J= 17 Hz), 7.20 (d, 1H, J= 17 Hz), 7.47 (d, 2H, J= 9 Hz), 7.68 (d, 2H, J= 9 Hz), 11.50 (s, 1H), 13.15 (s, 1H).

We claim:

1. A heterocyclic compound of formula I

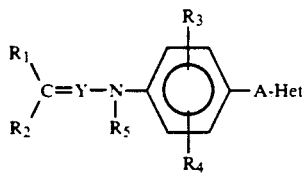

wherein Het represents one of the following groups:

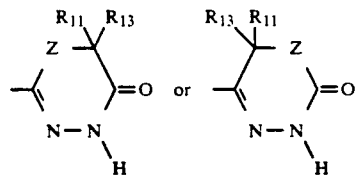

wherein $R_{11}$ and $R_{13}$ represent independently hydrogen or lower alkyl group, Z represents NH; A represents a valency bond, —CH=CH— or —CH$_2$—CH$_2$— group; $R_1$ and $R_2$ independently represent nitro, cyano, halogen, amino, carboxamido, phenyl, benzoyl, pyridyl, alkoxycarbonyl, alkanoyl or one of the following groups:

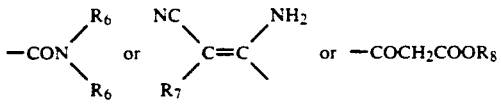

wherein $R_4$ represents hydrogen or lower alkyl group, $R_8$ represents lower alkyl, $R_7$ represents cyano or COOR$_{10}$, wherein $R_{10}$ represents hydrogen or lower alkyl, or $R_1$ and $R_2$ together form a substituted or unsubstituted 1-cyclohexylidene or 4-pyrazolidene ring; $R_3$, $R_4$, and $R_5$ represent independently hydrogen, hydroxy or lower alkyl group; Y represents N.

2. The compound according to claim 1, which is 6-[4-(1,1-dicyanomethylidenehydrazino)phenyl]-4,5-dihydro-5-methyl-1,2,4-triazin-3(2H)o ne.

3. The compound according to claim 1, which is 6-[4-(1,1-dicyanomethylidenehydrazino)phenyl]-4,5-dihydro-1,2,4-triazin-3(2H)one.

4. The compound according to claim 1, which is 2-[4-(1,1-dicyanomethylidenehydrazino)phenyl]-5,6-dihydro-1,3,4-triazin-5(4H)one.

5. The compound as claimed in claim 1 in the form of a pharmaceutically acceptable salt.

6. A pharmaceutical composition for treating congestive heart failure, said composition comprising an effective amount to treat congestive heart failure of a compound of the general formula I as claimed in claim 1, or a pharmaceutically acceptable salt together with a pharmaceutically acceptable carrier.

7. The pharmaceutical composition as claimed in claim 6, in unit dosage form.

8. The pharmaceutical composition as claimed in claim 6, in the form of coated tablets, dragees, capsules, suppositories, emulsions, suspensions or solutions.

9. The pharmaceutical composition as claimed in claim 6, additionally including solvents gel forming ingredients, dispersion forming ingredients, antioxidants, coloring agents, sweeteners or wetting agents.

10. A method for treating congestive heart failure in a mammalian organism, said method comprising administering an effective amount to treat congestive heart failure of a compound of formula I as claimed in claim 1 or a pharmaceutically acceptable salt to a mammaliam organism in need of such treatment.

* * * * *